(12) United States Patent
Althobity

(10) Patent No.: US 10,245,125 B2
(45) Date of Patent: Apr. 2, 2019

(54) METHOD FOR DUPLICATING A DENTURE

(71) Applicant: Imam Abdulrahman Bin Faisal University, Dammam (SA)

(72) Inventor: Ahmad Maniallah H. Althobity, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 10 days.

(21) Appl. No.: 15/601,203

(22) Filed: May 22, 2017

(65) Prior Publication Data

US 2018/0333236 A1    Nov. 22, 2018

(51) Int. Cl.
| | |
|---|---|
| A61C 13/087 | (2006.01) |
| A61C 13/20 | (2006.01) |
| B32B 27/26 | (2006.01) |
| A61C 13/08 | (2006.01) |
| A61C 8/00 | (2006.01) |
| A61C 13/34 | (2006.01) |
| A61C 13/00 | (2006.01) |
| A61C 9/00 | (2006.01) |
| B32B 27/28 | (2006.01) |

(52) U.S. Cl.
CPC .......... *A61C 13/081* (2013.01); *A61C 8/0001* (2013.01); *A61C 13/0006* (2013.01); *A61C 13/087* (2013.01); *A61C 13/34* (2013.01); *A61C 8/0095* (2013.01); *A61C 9/0006* (2013.01); *B32B 27/26* (2013.01); *B32B 27/28* (2013.01)

(58) Field of Classification Search
CPC ..... A61C 8/0001; A61C 13/01; A61C 13/081; A61C 13/04; A61K 6/10; A61K 6/0023
USPC .............. 264/17, 18; 523/109, 120; 433/213
See application file for complete search history.

(56) References Cited

U.S. PATENT DOCUMENTS

| 4,521,193 A | 6/1985 | Cialone |
| 5,569,036 A * | 10/1996 | Goldiner ............ A61C 13/0001 433/168.1 |
| 5,607,626 A | 3/1997 | Palazzolo |
| 5,711,668 A | 1/1998 | Huestis |

(Continued)

FOREIGN PATENT DOCUMENTS

EP    0 790 039 A1    8/1997

OTHER PUBLICATIONS

Steven Soo, et al., "Complete denture copy technique—A practical application", Singapore Dental Journal, vol. 35, 2014, pp. 65-70.

(Continued)

*Primary Examiner* — Tae H Yoon
(74) *Attorney, Agent, or Firm* — Oblon, McClelland, Maier & Neustadt, L.L.P.

(57) ABSTRACT

The fabrication of an implant-supported fixed complete denture involves multiple clinical and laboratory steps. One of the main steps is to provide the patient with an interim fixed prosthesis to evaluate the patient's esthetic and function al needs as well as to enhance the patient's psychology before proceeding to the definitive prosthesis. Different techniques for fabricating interim prostheses have been described in the literature. This disclosure describes a method of fabricating an implant-supported fixed interim prosthesis using self-curing acrylic resin. The interim prosthesis may be used as a blueprint for the definitive implant-supported hybrid prosthesis.

20 Claims, 13 Drawing Sheets

(56) References Cited

U.S. PATENT DOCUMENTS

2002/0163096 A1* 11/2002 Price ................. A61C 13/04
264/16

OTHER PUBLICATIONS

Sandra L. McCarthy, "Fabrication of a Duplicate Denture From an Existing Complete Denture", Journal of Prosthodontics. vol. 4, No. 1, Apr. 1995, pp. 54-57 (Abstract only).

Mustapha Rammal, et al., "Single appointment interim partial denture for a patient with a self-maintained provisional", General Dentistry, vol. 62, No. 4, Jul. 2014, pp. 20-23 (Abstract only).

Ahmad M. Al-Thobity, "Fabrication of an Implant-Supported Fixed Interim Prosthesis Using a Duplicate Denture: An Alternative Technique", Journal of Prosthodontics, ACP American College of Prosthodontists, 2016, pp. 1-5.

* cited by examiner

METHOD FOR DUPLICATING A DENTURE

STATEMENT REGARDING PRIOR DISCLOSURES BY THE INVENTORS

Aspects of this technology are described in an article "Fabrication of an Implant-Supported Fixed Interim Prosthesis Using a Duplicate Denture: An Alternative Technique" by Ahmad M. Al-Thobity in Journal of Prosthodontics, 2016, 1-5, which is incorporated herein by reference in its entirety.

BACKGROUND

Field of the Disclosure

This disclosure relates to a method for duplicating a worn denture which can be a full or partial denture.

Description of the Related Art

The use of dental implants to rehabilitate completely edentulous patients is a multi-step procedure that requires precise surgical and prosthetic management. A healing period of 3 to 6 months is required after implant placement to allow for osseointegration. During this period, the existing prosthesis can be relined, or transitional complete dentures can be constructed (Bränemark P-I, Bryonia U, Adell R, et al.: Intra-osseous anchorage of dental prostheses. I. Experimental studies. Scand J Plast Reconstr Surg 1969, 3:81-100; Bránemark P I: Osseointegration and its experimental background. J Prosthet Dent 1983, 50:399-410; and Brancmark P I, Zarb G, Albrektsson T: Tissue-Integrated Prosthesis—Osseointegration in Clinical Dentistry. Chicago, Quintessence, 1985, each incorporated herein by reference in their entirety). Transitional dentures must maintain the patient's occlusal vertical dimension (OVD) and meet the patient's needs (Balshi T J: The Biotes conversion prosthesis: a provisional fixed prosthesis supported by osseointegrated titanium fixtures for restoration of the edentulous jaw. Quintessence Int 1985, 16:667-677, incorporated herein by reference in its entirety).

After the osseointegration period, an implant-supported fixed interim prosthesis can be constructed to allow soft-tissue contouring and to determine the design of the definitive fixed prosthesis. Different techniques can be used to construct an implant-supported fixed interim prosthesis after the second surgical stage (Balshi T J, Wolfinger G J: Conversion prosthesis: a transitional fixed implant-supported prosthesis for an edentulous arch—a technical note. Int J Oral Maxillofac Implants 1996, 11:106-111; Moskowitz E M, Sheridan J J, Celenza F, et al. Essix appliances. Provisional anterior prosthesis for pre and post implant patients. NY State Dent J 1997, 63:32-35; Cibirka R M, Linebaugh M L: The fixed/detachable implant provisional prosthesis. J Prosthodont 1997, 6:149-152; and Babbush C A: Provisional implants: surgical and prosthetic aspects. Implant Dent 2001, 10:113-120, each incorporated herein by reference in their entirety). One such technique is to convert the transitional denture into such prosthesis. The drawback of this technique is that the denture teeth may pop out of the prosthesis during mastication. In addition, if the interim prosthesis is broken, the patient will not have a backup prosthesis for urgent situations.

Different techniques for fabricating a duplicate dental prosthesis out of complete dentures have been reported (Nassif J. Jumbelic R: Duplicating maxillary complete dentures. J Prosthet Dent 1984, 52:755-759; Wagner A G: A temporary replacement for an existing complete denture. J Prosthet Dent 1987, 58:522-525; Singer I L: The "zipper" technique for duplicating dentures: final impressions, replica dentures, and a complete denture splint. J Prosthet Dent 1975, 33:582-590; Hansen P A, Kim E: A provisional fixed partial denture for an implant prosthesis. Gen Dent 2010, 8:26-29; Afshari F S, Hallos M B, Knoernschild K L: An alternative approach in fabrication of fixed complete dentures using a duplicate denture. J Prosthodont 2012, 21:569-572; and Bidra A S: Chair-side fabrication of a fixed implant-supported prosthesis in an edentulous mandible flora a diagnostic wax-up: a clinical report. J Oral Implantol 2012, 38:291-297, each incorporated herein by reference in their entirety). Afshar et al. duplicated a conventional mandibular complete denture into a radiographic guide. After that, the conventional denture vas converted to a fixed complete denture with immediately loaded dental implants. After the implants had osseointegrated, the radiographic guide was used to transfer the OVD record and tooth position to the articulator predetermined in the conversion prosthesis. Afshari's duplicate denture was used only to verify the OVD and tooth and implant positions. Bidra studied a chairside duplicated dental prosthesis using a putty index on the working cast (Bidra A S: Chair-side fabrication of a fixed implant-supported prosthesis in an edentulous mandible from a diagnostic wax-up: a clinical report. J Oral Implantol 2012, 38:291-297, incorporated herein by reference in their entirety). Tooth-colored resin was poured into the index, and after the resin had set, self-curing denture base resin was poured into the index.

In view of the foregoing, it is an objective of the present disclosure to develop a method for forming a duplicate denture which can address patients' esthetic and functional concerns. It is a further objective to provide duplicate dentures as backup dentures for patients who are waiting for their definitive dentures.

SUMMARY OF THE DISCLOSURE

A first aspect of the disclosure relates to a process for forming a duplicate denture, the process comprising: (i) obtaining an intermediate denture comprising teeth and a gum portion; (ii) removing the teeth of the intermediate denture thereby exposing a part of the gum portion: (iii) applying an adhesive to the exposed part of the gum portion; (iv) filling a first portion of a mold of an original denture with a first resin: (v) placing the gum portion of the intermediate denture into a second portion of the mold; (vi) placing the first portion and the second portion of the mold in a contiguous matching relationship thereby contacting the exposed part of the gum portion with the first resin, and (vi) polymerizing the first resin thereby forming a duplicate denture.

In one embodiment, the teeth of the intermediate denture are removed to a gum line of the intermediate denture, and the exposed part of the gum portion comprises a plurality of concave sections angled away from the gum portion.

In one embodiment, the plurality of concave sections comprises a plurality of grooves.

In one embodiment, an average distance between each groove is 1-5 mm.

In one embodiment, each groove is V-shaped or U-shaped.

In one embodiment, the original denture is a full denture or a partial denture.

In one embodiment, the adhesive comprises methacrylate monomers.

In one embodiment, the intermediate denture is made by a process comprising filling the mold with a second resin; and polymerizing the second resin thereby forming the intermediate denture.

In one embodiment, the first resin and the second resin comprise an acrylate, nylon, or both.

In one embodiment, the first resin and the second resin comprise the acrylate.

In one embodiment, the first resin and the second resin are independently selected from the group consisting of a heat-curing resin, a self-curing resin, a light-curing resin, and a microwave-curing resin.

In one embodiment, the first resin is the self-curing resin.

In one embodiment, the second resin is the self-curing resin.

In, one embodiment, the mold is formed by a process comprising: (i) embedding a tooth portion of the original denture in a first molding material; (ii) embedding a gum portion of the original denture in a second molding material; and (iii) setting the first molding material and the second molding material thereby forming the mold.

In one embodiment, the first molding material and the second molding material comprise at least one selected from the group consisting of zinc oxide eugenol, alginate, a polyether, and a silicone.

In one embodiment, the first molding material and the second molding material comprise silicone.

In one embodiment, the silicone is condensation-cured silicone.

In one embodiment, the first molding material is placed in a first half of a flask or a first impression tray, and the second molding material is placed in a second half of the flask or a second impression tray.

In one embodiment, the flask is a Lang duplicator flask.

In one embodiment, the process further comprises closing the Lang duplicator flask before the setting of the first molding material and the second molding material.

In one embodiment, the process further comprises cutting an incisal edge of at least one tooth in the duplicate denture thereby forming a cut enamel portion; and applying a third resin and optionally a fourth resin to the cut enamel portion thereby smoothing the at least one tooth.

In one embodiment, where the fourth resin is present, the process further comprises mixing the third resin with the fourth resin prior to the application.

In one embodiment, the third resin and the fourth resin comprise an acrylate, nylon, or both.

In one embodiment, the third resin and the fourth resin comprise the acrylate.

BRIEF DESCRIPTION OF THE DRAWINGS

A more complete appreciation of the disclosure and a any of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
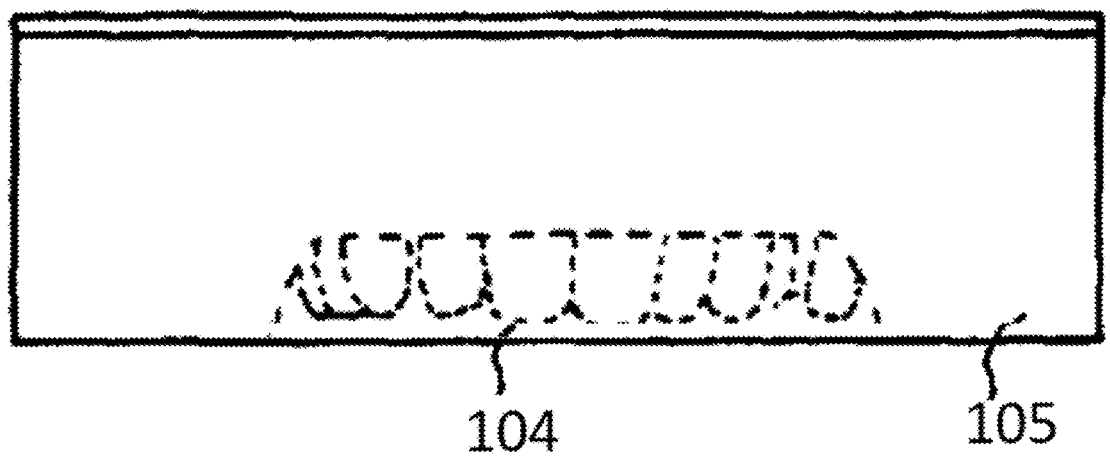
FIG. 1 shows the tooth portion of the original denture in the first molding material.

Embodiments of the present disclosure will now be described more fully hereinafter with reference to the accompanying drawings, in which some, but not all embodiments of the disclosure are shown.

As used herein, the words "a", "an", and the like carry the meaning of "one or, more". Within the description of this disclosure, where a numerical limit or range is stated, the endpoints are included unless stated otherwise. Also, all values and subranges within a numerical limit or range are specifically included as if explicitly written out.

The method may be carried out in a present-day dental clinic and/or a dental studio and thus will be described with reference to apparatus presently used and found in the dental clinic and/or the dental studio. In some embodiments, the method is carried out on an industrial level.

The materials (e.g., resins and adhesives) indicated for use in forming the duplicate denture are materials presently on sale and known to specialists in this field, but other materials with equivalent functions can be devised and used without departing from the scope of the present disclosure.

The original denture 108 worn by the patient may be a regular complete denture, which is supported by the gums and is not, supported by implants, and contains a tooth portion 104, a gum portion 107 which includes the gums and a palate portion in contact with the patient's palate. In some embodiments, the original denture 108 is supported or retained by implants. In some embodiments, the original denture 108 is a partial denture.

While the method may be practiced in creating a partial denture, a complete upper denture, or a complete lower denture, only the complete upper denture is depicted since no fundamental difference exists in the application of the method for the types of denture. The complete upper denture and the complete lower denture may be constructed during different dental appointments or constructed during the same dental appointment. The coordination of the upper denture to the lower denture is often of vital importance in meeting the dental needs of a patient.

The duplicate denture 200 may be a regular complete denture or an interim implant-supported denture that is attached to the implants. The conventional technique for fabricating fixed interim implant-supported denture for edentulous patients involves making a transitional complete denture into a fixed interim denture. The disadvantages of this approach are the denture teeth may pop out of the denture and result in breakages that are difficult to repair. Thus, a duplicate denture 200 may be needed. The patient may use such dentures before the definitive denture is made.

In these cases, the dentist may use the duplicate denture 200 as a blueprint for the definitive denture, which may be a fixed or removable implant-supported denture, or an implant-retained denture. In other embodiments, the duplicate denture 200 is the definitive denture.

In a preferred embodiment, the duplicate denture 200 is an interim implant-supported denture and the original denture 108 is a regular complete denture supported by the patient's gums. In this embodiment, the duplicate denture 200 may have the palate portion removed.

Figure 2:
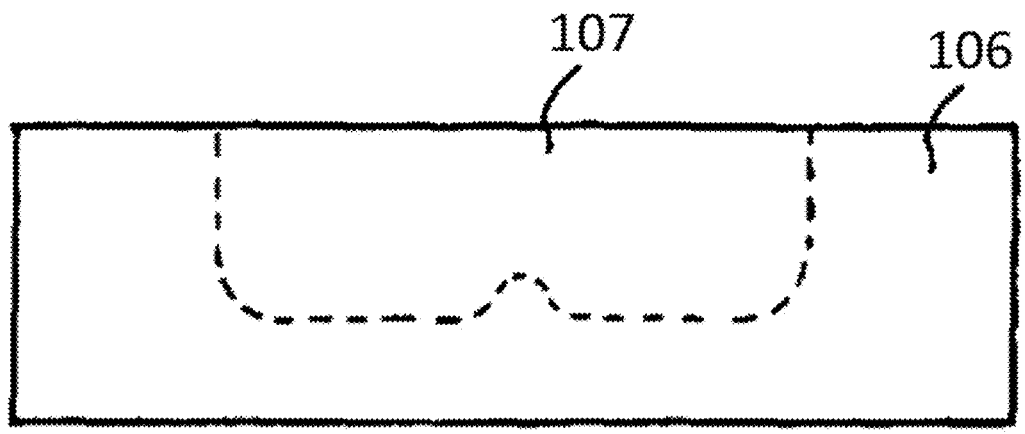
FIG. 2 shows the gum portion of the original denture in the second molding material.

In the making of an impression of the original denture 108, a tooth portion 104 of the original denture 108 is embedded in a first molding material 105 (as shown in FIG. 1), and the gum portion 107 of the original denture 108 is embedded in a second molding material 106 (as shown in FIG. 2). The term "tooth portion" 104 refers to the portion beginning on an imaginary plane crossing the denture at the height at which the teeth emerge from the gum. Consequently, the tooth portion 104 also includes the parts of the gum located between the teeth.

The first and second molding materials may include zinc oxide eugenol, alginate, agar, polysulfide, a polyether, and a silicone. Preferably, the first and second molding materials include silicone such as polyvinyl siloxane, polymethylhydrosiloxane, and polydimethyl siloxane (hydroxy terminated). The silicone may be condensation-cured or addition-cured. Preferably, the silicone is condensation-cured.

The first molding material 105 and the second molding material 106 may be the same or different. For example, the first molding material 105 may be silicone, and the second molding material 106 is agar. Preferably, both the first molding material 105 and the second molding material 106 are the same.

The mold may be prepared with or without a flask or impression trays. In some embodiments, the first molding material 105 may be placed in a first half of a flask or a first impression tray, and the second molding material 106 may be placed in a second half of the flask or a second impression tray. The flask may be an Atlas denture flask or a Lang duplicator flask 112.

In a preferred embodiment, a Lang duplicator flask 112 is used to minimize the dimensional change of the mold. The Lang duplicator flask 112 typically includes an upper half shell 109 and a lower half shell 110 which close together along a common plane 111.

Figure 6:
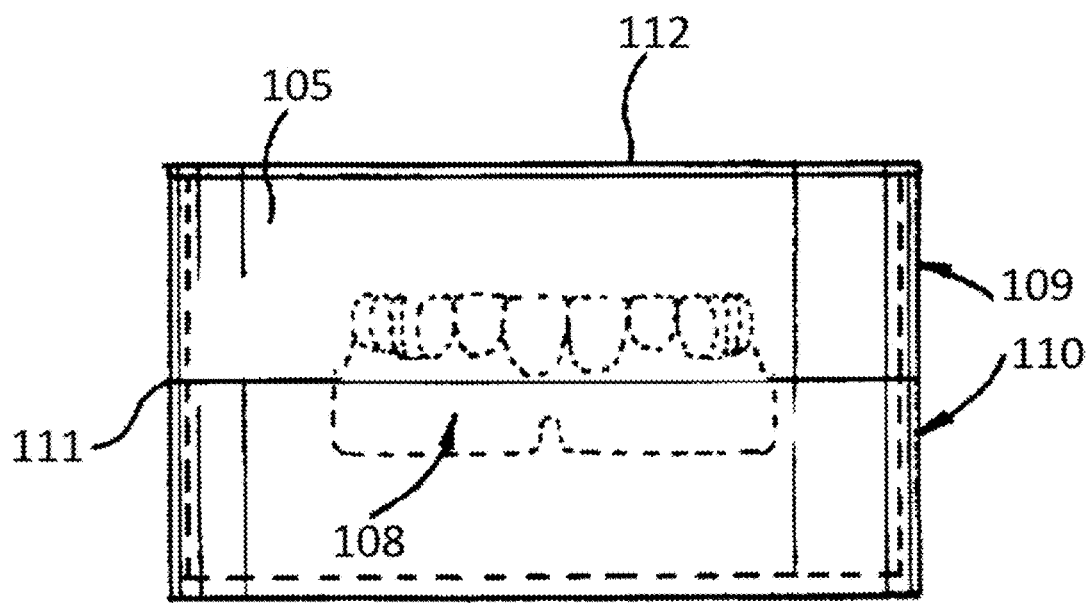
FIG. 6 shows the original denture in the mold.

In some embodiments, the Lang duplicator flask 112 is closed after being filled with the molding materials (as shown in FIG. 6). After which, the Lang duplicator flask 112 is placed in a dental press to press out any excess molding materials and to ensure the molding materials conform to the shape of the original denture 108. An applied pressure may be in range of more than 1 atm to 6 atm, 1.5-5 atm, or 2-3 atm. A duration of the pressing may be in a range of 5-50 minutes, 10-30 minutes, or 15-20 minutes.

After the molding materials have hardened/set, the Lang duplicator flask 112 is removed from the dental press. The Lang duplicator flask 112 is opened and the original denture 108 is removed and returned to the patient. The impressions of the tooth portion 104 and the gum portion 107 of the original denture 108 are thus left in the mold.

In some embodiments, the impression tray is used in the making of the mold. The impression tray may be available commercially (e.g., a stock tray) or custom-made (e.g., a special tray). The impression tray may be perforated to allow the impression material to run through the holes and increase the bonding of the impression material to the tray when set. The impression tray may be disposable and for single-use, or be capable of being disinfected and reused.

The impression tray may be rounded, designed to fit the mouths of patients with no remaining teeth, or squared, designed to fit patients with some remaining teeth. The impression tray may be full arch, covering all the teeth in either the upper or lower jaw in one impression, or it can be a partial coverage tray, designed to fit over 3-6, 3-5, or about 3 teeth.

The impression of the original denture 108 in the mold may be filled with a second resin which is then polymerized thereby forming the intermediate denture 100 with teeth 101 and a gum portion 102.

Commercially available resins may be used with the presently disclosed method. Such resins may include, without limitation, Valplast®, Flexite®, DuraFlex™, ALIKE™, and TCS®. Valplast®, Flexite®, and DuraFlex™ are flexible nylon-based thermoplastic materials, and ALIKE™ and TCS® are acrylate-based materials. The resins described herein (i.e., the first, second, third; and fourth resins) may comprise nylon, polytetrafluoroethylene, polyester, acrylate, or mixtures thereof. Dentures made from a thermoplastic, such as nylon, are flexible and thus translate to a more comfortable experience with chewing and speaking. One of ordinary skill in the art readily appreciates that the thermoplastic can be molded into the shape of a denture by following the manufacturer's instructions.

In a preferred embodiment, the resin comprises an acrylate. For example, the resin may comprise reacted forms (e.g., polymers) of methyl methacrylate, ethyl methacrylate, butyl methacrylate, n-butyl methacrylate, i-butylmethacrylate, hexylmethacrylate, dicyclopentenylmethacrylate, tetrahydrofurfurylmethacrylate, 2-hydroxyethylmethacrylate, glycidylmethacrylate, laurylmethacrylate, cyclohexylmethacrylate, benzylmethacrylate, allylmethacrylate, 2-ethoxyethyl methacrylate, methoxy polyethylene glycolmethacrylate, glycerol methacrylate, isobornyl methacrylate, methyl acrylate, ethyl acrylate, butyl acrylate, n-butyl acrylate, i-butylacrylate, hexylacrylate, dicyclopentenylacrylate, tetrahydrofurfurylacrylate, 2-hydroxyethylacrylate, glycidylacrylate, laurylacrylate, cyclohexylacrylate, benzylacrylate, allylacrylate, 2-ethoxyethyl acrylate, methoxy polyethylene glycolacrylate, glycerol acrylate, and isobornyl acrylate. The resin may also include a copolymer such as methyl methacrylate-ethyl methacrylate copolymer. The resin may also include cross-linked polymers such as cross-linked polymethyl methacrylate, and cross-linked polyethyl methacrylate. The resin may further include nitrogen-containing compounds in reacted form of 2-(N,N-dimethylamino)ethylmethacrylate, N-methylolmethacrylamide, and diacetonemethacrylamide. The resin may further include silane compounds in reacted form of gamma-methacryloyloxypropyl trimethoxysilane, and gamma-methacryloyloxypropyl triethoxysilane. The resin may include multi-functional resins in reacted form of 2-hydroxy-3-acryloyloxypropyl methacrylate, hydroxypivalic acid neopentyl glycol dimethacrylate, ethylene glycol dimethacrylate, diethylene glycol dimethacrylate, triethylene glycol dimethacrylate, butylene glycol dimethacrylate, pentaerythritol tetra(meth)acrylate, and ditrimethylolpropane tetra(meth)acrylate.

The resins comprising acrylate for the manufacture of dentures are made up of liquids and powders. Such resins are commonly referred to as "acrylic resins". The liquids contain monomers while the powders are prepolymerized polymers. The liquids and the powders are mixed together at a ratio instructed by the manufacturer and then cured. In the context of the present disclosure, "curing" refers to a process during which the resin polymerizes and forms either a part or the entirety of the denture (either the intermediate or duplicate denture). The resins can be heat-curing resins, self-curing resins, light-curing resins, or microwave-curing resins. Preferably, the resins are self-curing resins to eliminate the need to provide curing conditions as is commonly done with a curing unit, or to adjust the temperature, humidity, or light intensity. Self-curing is polymerization caused by chemical catalysis rather than applying heat or light. In some embodiments, self-curing resins result in a porous denture which may be easily stained by foods, such as coffee and tea, and smoking. Bohra et al. compared the color stability of heat- and self-cured acrylic resins using a spectrophotometer and reported more color variations when self-cured denture base resin was used (Bohra P K, Ganesh P R, Reddy M M, et al. Color stability of heat and cold cure acrylic resins. J Clin Diagn Res 2015, 9:12-15, incorporated herein by reference in its entirety). The denture may have a porosity of 5-20%, 5-15%, or 5-10%. The porosity of the denture may be determined by weighing the denture in air and then in water, and calculating the porosity using the following equations (M Bafile, N Gerald, Graser, M L Myers, E K Li. Porosity of denture resin cured by microwave energy. J Prosthet Dent. 1991; 66:269-274, incorporated herein by reference in its entirety).

$$W_a = g(d_r - d_a)(v_{sp} - v_{ip}) \quad (1)$$

$$W_w = g(d_r - d_w)(v_{sp} - v_{ip}) + g(d_a - d_w)v_{ip} \quad (2)$$

$$\text{Porosity } (\%) = v_{ip}/v_{sp} \times 100\% \quad (3)$$

where $W_a$ is the weight of the denture in air,
$W_w$ is the weight of the denture in water,
g is the gravitational constant (9.8066 m/sec$^2$),
$d_r$ is the density of acrylic resin (1,1986 kg/m$^3$),
$d_a$ is the density of air (1.23 kg/m$^3$),
$d_w$ is the density of water (1,000 kg/m$^3$),
$v_{sp}$ is the volume of the denture, and
$v_{ip}$ is the internal porosity volume.

In some embodiments, the self-curing resins are cured under pressure to reduce the porosity of the denture. For example, the Lang duplicator flask 112 may be pressurized with a hydraulic press pressure pot at the aforementioned pressure for the aforementioned duration. The porosity of the denture after pressing may be less than 20%, 10%, or 5%.

In one embodiment, the resins are heat-curing resins. Heat-activated curing includes applying heat to the mold via a hot-water bath, heating element, or heat lamps causing the polymerization of the resin inside the mold. The polymerization may take place in a duration of 1-30 minutes, 3-20 minutes, or 5-10 minutes, at a temperature of 80-130° C., 90-120° C., or 105-110° C., and at the aforementioned pressures. A type of apparatus commercially available for heat polymerization is IVOMAT manufactured by Ivoclar.

In one embodiment, the resins are light-curing resins. A light-based curing is a curing process in which light is used to create a photochemical reaction that causes the polymerization of the resin inside the mold. The light used for curing the resin is preferably visible light (e.g., one with a wavelength of 400-700 nm, 400-600 nm, or 400-550 nm). An LED, a halogen lamp, an arc light, a xenon lamp, or a combination thereof may be used for irradiation of visible light. A photopolymerizable resin is Licuplast, a known polymethylmethacrylate composition which polymerizes in 10-30 minutes, 15-25 minutes, or 18-22 minutes at a 350 to 500 nm light wavelength. A photopolymerizing apparatus which can be used is TRIAD 2000.

The second resin cures in a shape that completely fills or substantially fills the impression in the mold, which directly correlates to the spatial volume and shape of the patient's worn denture. The second resin is in a shade of pink, for example, G1, G2, G3, G4, G5, GOL, and GOD shades of the VITA shade guide. As a result, the teeth 101 and the gum portion 102 of the intermediate denture 200 are in a shade of pink. The color shade of the second resin is chosen to match the color of the patient's gums 1201. The intermediate denture 100 represents the original denture 108 in its entirety (i.e., including the crown areas of each dental tooth, surfaces of a patient's soft tissues in contact with the worn denture, and undercuts along the patient's edentulous ridge).

Figure 3:
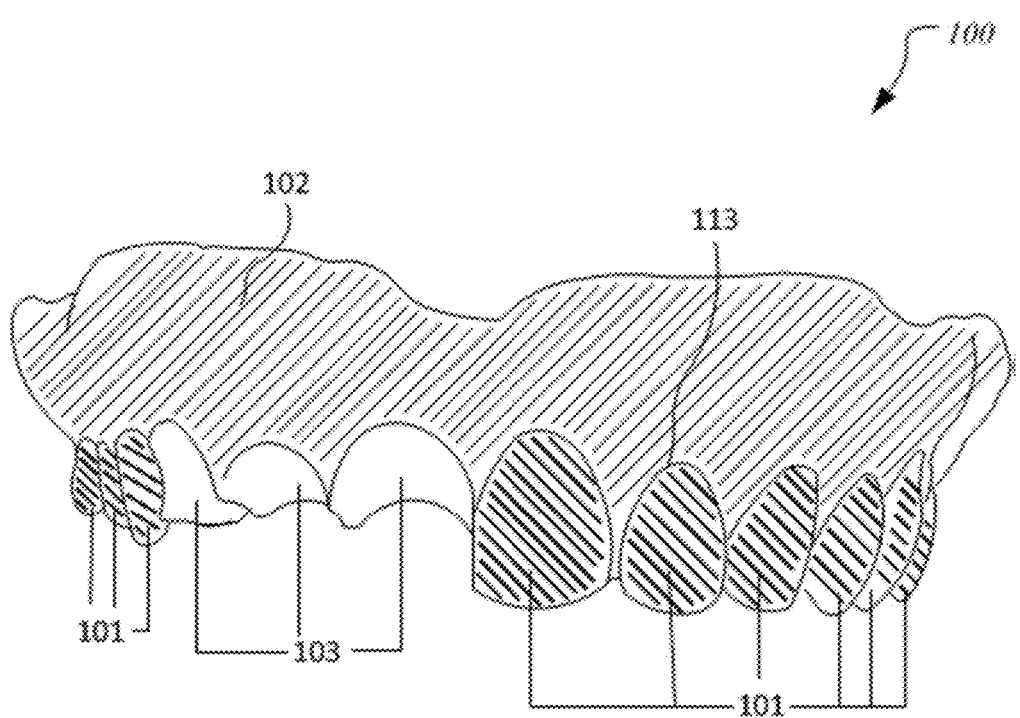
FIG. 3 shows the intermediate denture after removing some of the teeth.
Figure 4:
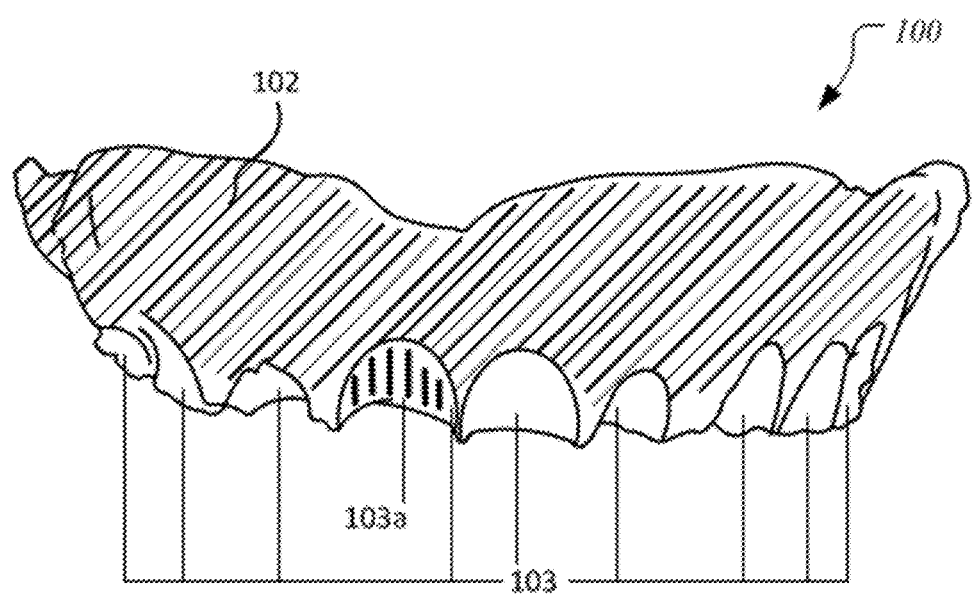
FIG. 4 shows the intermediate denture after removing all of the teeth.

FIG. 3 shows that the teeth 101 of the intermediate denture 100 are cut to the gum margin 113 in the front and lingual surfaces of the intermediate denture 100 and then removed thereby exposing parts 103 of the gum portion 102 that are hidden by the teeth 101. FIGS. 3 and 4 show the exposed parts 103 of the gum portion 102 are unshaded and comprise a plurality of concave sections angled away from the gum portion 102. The teeth 101 may be cut to not more than 1.5 mm, not more than 1.2 mm, not more than 1 mm, not more than 0.8 mm, or not more than 0.5 mm from either side of the gum margin 113. A tool, such as a fingernail drill, a crafting rotary tool, or an acrylic trimmer, may be used to remove the teeth from the intermediate denture 100.

Each concave section may independently comprise a plurality of grooves 103a. FIG. 4 shows that the grooves 103a run from the front of the concave section (i.e., the side which is nearer the patient's lips) to the back of the concave section. In some embodiments, the grooves may be oriented substantially parallel to the gum margin 113 (i.e., at least 60%, at least 80%, or at least 90% of the grooves may be aligned at no more than 10°, preferably no more than 7°, more preferably no more than 5° relative to the gum margin). The presence of the grooves 103a increases the contact surface between the concave sections and the teeth of the duplicate denture and thus reduces the potential of the denture teeth popping out when the denture is manipulated to an implant-supported denture. The contact surface may increase by 5-80%, 10-60%, or 20-40%, relative to a surface area of a concave section prior to marking of the grooves 103a. The grooves 103a may intersect at least one other groove, or may be substantially parallel to one another (i.e., the majority of the grooves are separated by substantially the same distance). For example, at least 60%, preferably at least 80%, more preferably at least 90% of the grooves 103a may be aligned at no more than 10°, preferably no more than 7°, more preferably no more than 5°, relative to the adjacent grooves. An average distance between the grooves 103a may range from 1-5 mm, 1.5-4 mm, or 2-3 mm. Each groove 103a may be in a shape of a "V" or a "U". An average width of each groove 103a, measured from the widest part of each groove 103a, may be in a range of 0.01-2 mm, 0.01-1.5 mm, 0.01-1 mm, 0.01-0.5 mm, or 0.01-0.1 mm. An average depth of each groove 103a may be in a range of 0.01-2 mm, 0.01-1 mm, or 0.01-0.5 mm. An average length of each groove 103a may be in a range of 1-5 mm, 1.5-4 mm, or 2-3 mm. In addition to the tools described herein, a plastic cutter may be used to score the concave sections thereby creating the plurality of grooves 103a.

The first portion of the mold contains the impression of the tooth portion 104 which is filled with a first resin. An adhesive is applied to the exposed parts 103 of the gum portion 102 of the intermediate denture 100 to receive and bond with the first resin. As the adherence of the resin to the gum portion takes place by chemical adhesion between the first resin and the exposed part of the gum, the adhesive contains a polymerizable monomer. Exemplary monomers include, without limitation, methyl methacrylate, ethyl methacrylate, butyl methacrylate, n-butyl methacrylate, i-butylmethacrylate, hexylmethacrylate, dicyclopentenylmethacrylate, tetrahydrofurfurylmethacrylate, 2-hydroxyethylmethacrylate, glycidylmethacrylate, laurylmethacrylate, cyclohexylmethacrylate, benzylmethacrylate, allylmethacrylate, 2-ethoxyethyl methacrylate, methoxy polyethylene glycolmethacrylate, glycerol methacrylate, isobornyl methacrylate, and mixtures thereof.

The color of the first, third, and fourth resins is a shade of white because these resins, when cured, form the teeth of the duplicate denture. For example, according to the VITA classical shade guide, natural shades of teeth include, B1, A1, B2, D2, A2, C1, C2, D4, A3, D3, B3, A3.5, B4, C3, A4, C4, in the order of increasing darkness, with B1 being the lightest shade. The color of the first, third, and fourth resins may be in a bleached state such as 0M1, 0M2, and 0M3. The color of the first resin may be chosen to match the color of the existing teeth in the patient (in the case of a partial denture).

Figure 5:
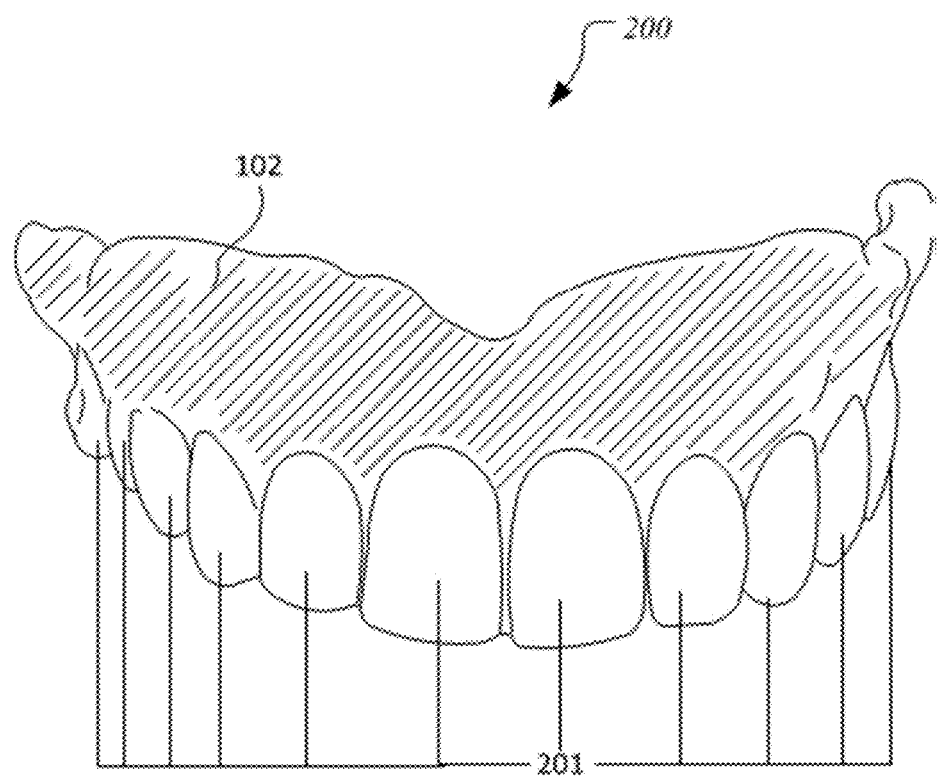
FIG. 5 shows a complete upper duplicate denture.

The gum portion 102 of the intermediate denture 100 is placed back into the impression of the gum portion 107 in the second portion of the mold. Subsequently, the Lang duplicator flask 112 is closed such that the first portion and the second portion of the mold is in a contiguous matching relationship thereby contacting the exposed parts 103 of the gum portion 102 with the first resin. The mold may be pressed with a hydraulic press pressure pot at the aforementioned pressures and/or duration. The first resin is polymerized to form the teeth which adhere to the gum portion 102 and to form the duplicate denture 200 with teeth 201 in a shade of white. FIG. 5 shows the duplicate denture 200.

One advantage of this method is the ability to create the natural luster and translucency of teeth enamel in the teeth of the duplicate denture. The teeth in the conventional dentures are opaque entirely. In the context of the disclosure, the term "opaque" describes a material transmitting up to 10%, less than 7%, less than 4%, or less than 1% of the light impinged on the material; and the term "translucent" describes a material transmitting more than 10%, more than 20%, or more than 30%, and up to 70%, up to 60%, or up to 50% of the light impinged on the material. At least one anterior tooth may be cut back 0.1-2 mm, 0.4-1.5 mm, or 0.8-1.1 mm from the incisal edge 202 (i.e., the cutting edge of the anterior tooth) thereby forming bumps 203 on the edge of the tooth. The bumps 203 are then smoothed by applying a third resin with a lighter shade than the first resin. The third resin may appear translucent upon curing. The third resin may be applied with a dental composite placement instrument. The duplicate denture 200 may then be put back in the same mold for the curing of the third resin. In some embodiments, the aforementioned pressure is applied to the mold when the third resin is curing. In some embodiments, a fourth resin is used with the third resin, and a mixture of the third and fourth resins are applied over the bumps 203.

The resins may further include a filler to adjust the discharging force, improve the mechanical strength of the duplicate denture 200, and/or minimize the growth of microbes. The shape of the filler is not particularly limited. For example, the filler may be spherical or substantially spherical (e.g., oval or oblong shape). In other embodiments, the filler can be of any shape that provides the duplicate denture 200 with the aforementioned properties. In some embodiments, the filler is in the form of at least one shape such as a sphere, a rod, a cylinder, a rectangle, a triangle, a pentagon, a hexagon, a prism, a disk, a platelet, a flake, a cube, a cuboid, and an urchin (e.g., a globular particle possessing a spiky uneven surface). For the ease of handling of the resin, spherical fillers are preferred. The average particle diameter of the filler may be in a range of 0.001-50 µm, 0.01-10 µm, 0.1-1 µm, 0.2-0.5 µm. An average particle diameter, as used herein, refers to the average linear distance measured from a first point on the filler through the center of the filler to a second point directly across from the first point.

Examples of fillers include an inorganic filler and an antimicrobial agent. Examples of the inorganic filler include quartz, silica, alumina, silica-titania, silica-titania-barium oxide, silica-zirconia, silica-alumina, lanthanum glass, borosilicate glass, soda glass, barium glass, strontium glass, glass ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, strontium calcium fluoroaluminosilicate glass, tricalcium phosphate, dicalcium phosphate dihydrate, dicalcium phosphate anhydrous, pyrophosphate, hydroxyapatite, biphasic calcium phosphate, carbonated apatite, octacalcium phosphate, alumina, Bioglass®, Pyrex®, and combinations thereof. The content of the inorganic filler in the duplicate denture 200 is preferably 0.01-40 wt %, 0.1-30 wt %, 1-20 wt %, or 5-12 wt %, based on a total weight of the duplicate denture.

Microbes adhere to the conventional dentures and forms microbial colonies. In particular, denture wearers are particularly prone to oral thrush, a common condition due to *Candida albicans* fungus. Therefore, the duplicate denture 200 of this disclosure may include antimicrobial agents to prevent growth of the fungus and other harmful microbes. The antimicrobial agent may provide broad spectrum protection from bacterial or fungal infections inside a patient's mouth and aid in the cleaning process of dentures outside the mouth. The content of the antimicrobial agent in the duplicate denture 200 may be in a range of 0.1-25 wt %, 0.5-22 wt %, 1-20 wt %, 2-18 wt %, 5-15 wt %, 8-13 wt %, or 10-11 wt %, based on a total weight of the duplicate denture.

Exemplary antimicrobial agents include silver nanoparticles, titanium dioxide nanoparticles, a silicon compound, 2-amino-1,4-naphthoquinone, and/or 3-aminophenyl-2-hydroxy-1,4-naphthoquinone. The antimicrobial properties of silver nanoparticles stem from the chemical properties of $Ag^+$ and several mechanisms have been proposed to explain this effect. For example, silver ions form strong molecular bonds with other substances used by bacteria to respire, such as enzymes containing sulfur, nitrogen, and oxygen. When the $Ag^+$ ion forms a complex with these biomolecules, they are rendered inactive, depriving them of necessary activity and eventually leading to the death of the bacteria. Silver ions can also complex with bacterial DNA, impairing the ability of the microorganisms to reproduce. In some embodiments which include silver nanoparticles, the silver nanoparticles have an average diameter of 40-80 nm, 45-75 nm, 50-70 nm, or 55-65 nm.

Titanium dioxide nanoparticles have a broad spectrum of activity against microorganisms, including Gram-negative and Gram-positive bacteria and fungi, which may be of particular importance for multiple drug resistant strains. Further, the titanium dioxide nanoparticles exert a non-contact biocidal action. Therefore, no release of potentially toxic nanoparticles to the saliva is required to achieve disinfection capabilities. In some embodiments which include titanium dioxide particles, the titanium dioxide particles have an average diameter of 40-160 nm, 50-150 nm, 60-140 nm, 70-130 nm, 80-120 nm, or 90-110 nm.

Silicon compounds which may include silicon dioxide nanoparticles have been found to inhibit bacteria adherence to oral biofilms. A biofilm is any group of microorganisms in which cells stick to each other and often these cells adhere to a surface, such as a denture's surface. These adherent cells are frequently embedded within a self-produced matrix of extracellular polymeric substance (EPS). Biofilm extracellular polymeric substance is a polymeric conglomeration generally composed of extracellular DNA, proteins, and polysaccharides. Biofilms may form on living or non-living surfaces and can be prevalent in natural, industrial and hospital settings. Although not strictly having a toxic mechanism, the silicon compounds and nanoparticles may induce an unfavorable change in the biofilm to reduce the adhesion, and therefore inhibit the proliferation of bacteria and fungus. The silicon compound may include, but not limited to 3-(trimethoxysilyl)propyldimethyloctadecyl ammonium chloride, 3-(trimethoxysilyl)propylmethyldi(decyl) ammonium chloride, 3-chloropropyltrimethylsilane, octadecyltrimethoxysilane, perfluorooctyltriethoxysilane, ethyltrimethoxysilane, vinyltrimethoxysilane, or vinyltriacetoxysilane. Silicon dioxide nanoparticles may have an average diameter in a range of 10-30 nm, 12-28 nm, 15-25 nm, or 18-23 nm.

In some embodiments the antimicrobial agents described herein may be effective in treating bacteria and fungus including, but not limited to Gram-positive and Gram-negative bacteria, and candidal and non-candidal fungi. Gram-positive bacteria may include, but is not limited to pathogens such as *Staphylococcus aureus, Streptococcus pyogenes,* and *Clostridium botulinum*. Gram-negative bacteria may include, but is not limited to pathogens such as *Salmonella, Escherichia coli, Klebsiella, Haemophilus, Pseudomonas aeruginosa, Proteus,* and *Shigella dysenteriae*. Gram-negative bacteria are generally distinguished from Gram-positive by an additional protective cell membrane. Non-candidal oral mycoses that may be susceptible to the antimicrobial agents described herein may include, but are not limited to *aspergillus, cryptococcus, histoplasma, blastomyces, paracoccidioides,* and *zygomycota*.

In some embodiments, the antimicrobial agent may be mixed with the adhesive described herein and then applied onto the duplicate denture. The mixing of antimicrobial agent with the adhesive may be accomplished by mechanical mixing. The resulting mixture may be brushed or sprayed onto the duplicate denture. Alternative, the resulting mixture may be brushed or sprayed onto the impression of the mold and the denture is returned to the mold, and pressed. The antimicrobial agent may penetrate the denture (e.g., via the pores of the denture) or may persist on the surface of a denture to prevent or treat antimicrobial growth on the denture and/or surrounding tissues in the mouth.

Having generally described this disclosure, a further understanding can be obtained by reference to certain specific examples which are provided herein for purposes of illustration only and are not intended to be limiting unless otherwise specified.

EXAMPLE

A 64-year-old man reported to the postgraduate clinic at Rutgers School of Dental Medicine with a chief complaint of: "I don't like my teeth, and I can't chew efficiently." The patient was healthy and did not complain of any medical conditions. His dental history revealed multiple edentulous areas and multiple teeth that required extraction.

Preliminary impressions were made using alginate impression material. Facebow and centric relation (CR) records were made, and immediate complete dentures were constructed in the dental laboratory on a semi-adjustable articulator (Hanau WideView; WhipMix Corp., Louisville, Ky.). In the context of the present disclosure, the immediate complete dentures refer to dentures inserted in the patient's mouth on the same day as the removal of natural teeth. After the extractions, immediate complete dentures were adjusted, relined, and inserted into the patient's mouth. A surgical stent was fabricated and used as a guide for implant placement.

Three months later, six dental implants (two 3.8×11 mm implants and four 4.8×11 mm BL implants; Straumann, Andover, Mass.) were placed in the maxillary arch, and five implants were placed in the mandibular arch. After implant osseointegration, the duplicate denture, which was an interim fixed complete denture, was fabricated. After complete evaluation of the function and esthetics of the interim prosthesis, it was used as the blueprint for the definitive prosthesis.

In the laboratory, both immediate dentures were duplicated in a Lang denture duplicator flask (Lang Dental Manufacturing Co., Inc., Wheeling, Ill.) using a condensation silicone impression material (Aquasil Easy Mix Putty; Dentsply, York, Pa.) to make a mold for making the intermediate and duplicate dentures.

Self-curing acrylic resin containing pink fibers (resin material: Dentsply) was mixed in a powder/liquid ratio according to the manufacturer's instructions. The mixture was poured into the mold and then placed into the pressure pot until it was completely set in order to enhance the strength and reduce the porosity of the intermediate denture.

The teeth in the pink intermediate denture were cut back to the gingival margin, and then the powder/liquid mixture of the self-curing acrylic resin used for the interim prosthesis was set according to the manufacturer's instructions (ALIKE; GC America Inc., Alsip, Ill.). The exposed parts of the gum in the intermediate denture were wetted with methacrylate monomer to prepare them to receive the provisional acrylic resin mix.

The acrylic resin was mixed with shade A1 and poured directly into the mold. The gum portion of the intermediate denture was placed back into the mold to allow the new acrylic resin to fill intermediate denture. The mold containing the denture was then placed back into the pressure pot to enhance the strength and reduce the porosity of the duplicate denture formed. The duplicate denture was finished and polished using conventional methods.

In the patient's mouth, the duplicate denture was adjusted using a pressure-indicating paste for complete seating. Then, the occlusal vertical dimension (OVD) was evaluated and recorded using phonetic and esthetic techniques. After confirming the OVD, the CR position was evaluated, adjusted, and recorded using the bimanual technique.

Figure 7:
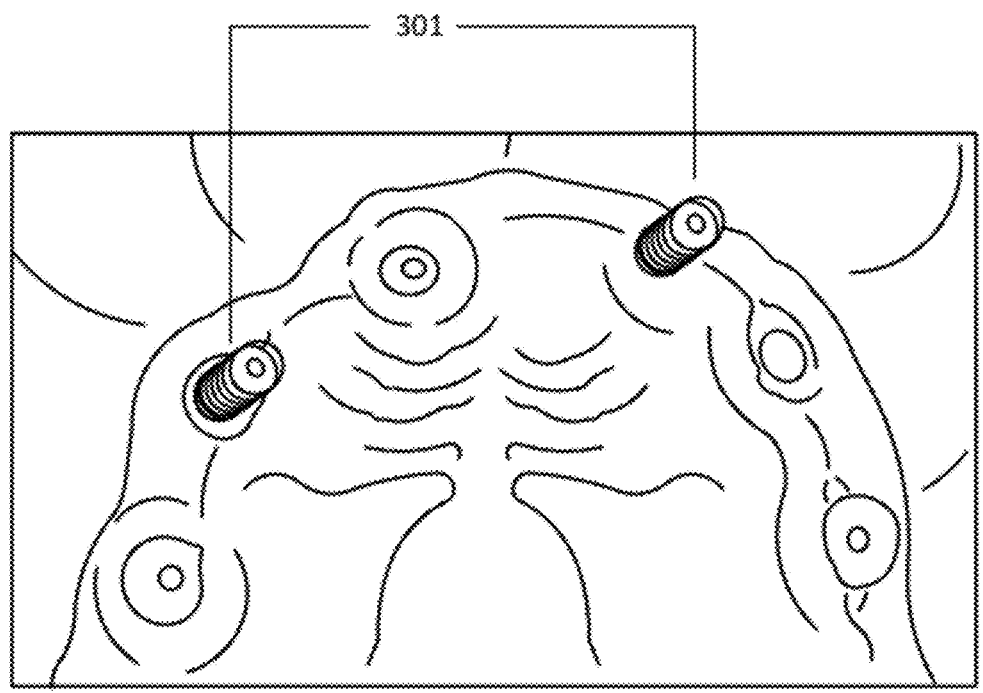
FIG. 7 shows two temporary abutments in the patient's gums.
Figure 8:
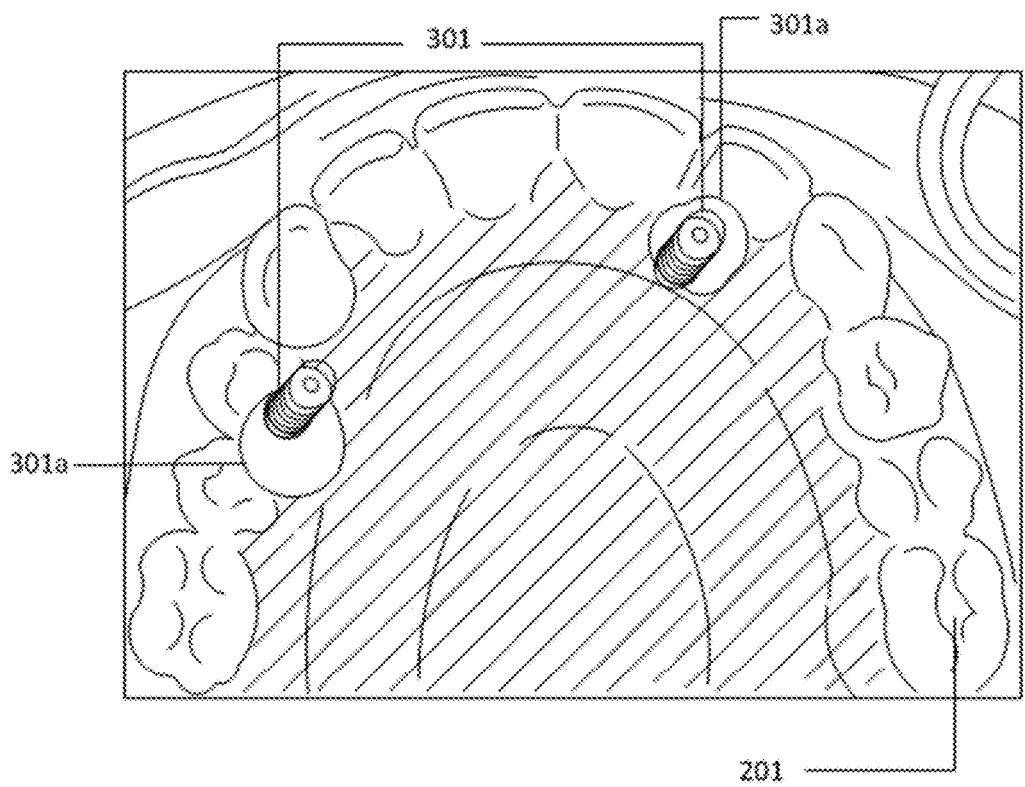
FIG. 8 shows the access holes in the duplicate denture correspond to the two temporary abutments shown in FIG. 7.

FIG. 7 shows two temporary titanium abutments 301 (RC temporary abutment Ø4.5 mm, NC temporary abutment Ø 3.5 mm; Straumann) are installed onto the implants in the maxillary right first premolar (#5) and the maxillary left lateral incisor (#10) areas. FIG. 8 shows two access holes 301a are created in the fitting surface of the duplicate denture to allow for picking up the abutments.

The two abutments 301 were picked up into the duplicate denture using self-curing acrylic resin by relining the resin around the abutments. The complete seating of the denture in the patient's mouth was checked while the acrylic resin set. The abutments 301 were then screwed out, and the denture was removed from the patient's mouth once the two abutments 301 were completely attached.

Figure 9:
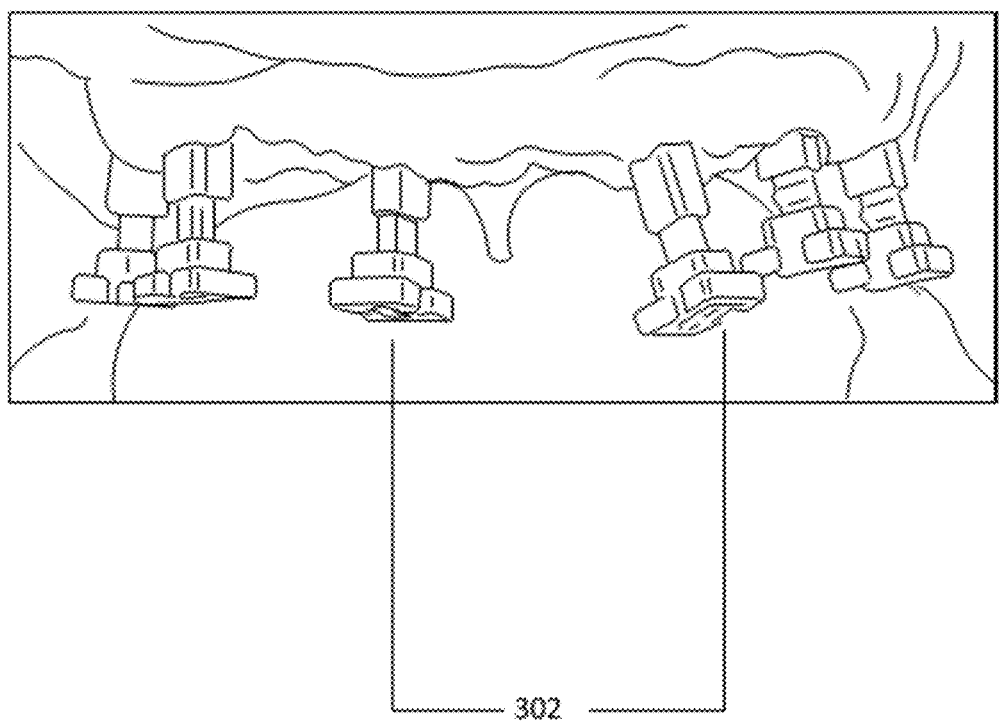
FIG. 9 shows an insert all close tray impression copings for polyvinyl si oxane impression.

FIG. 9 shows six closed-tray impression posts 302 (two NC and four RC impression posts with caps) are installed onto the dental implants in the maxillary lateral incisor, the maxillary first premolar, and the maxillary first molar areas.

The maxillary implant-level final impression was made with a vinylpolysiloxane (VPS) material (Extrude; Kerr, Orange, Calif.). All of the impression copings were screwed out of the patient's mouth and attached to the implant analogs (NC and RC implant analogs), and then inserted into their original positions in the final impression.

The final impression was poured using a type IV low-expansion dental stone (Fujirock EP; GC America, Alsip, Ill.) to produce the maxillary master cast.

Figure 10:
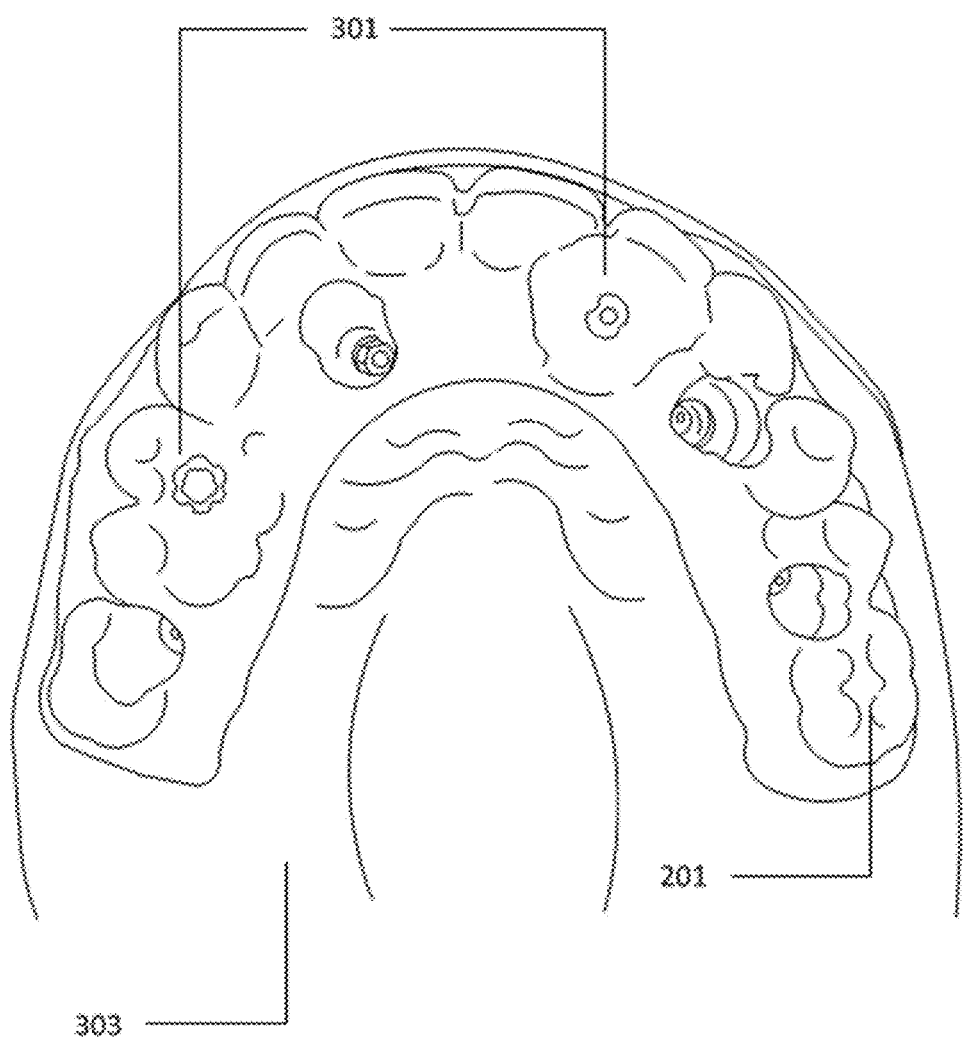
FIG. 10 shows the duplicate denture inserted into a master cast with two abutments.

In a dental laboratory, all of the flanges and the palate part of the duplicate denture were cut out. FIG. 10 shows the duplicate denture is then seated on the master cast 303 by screwing the two temporary abutments 301 into it. After that, access holes were created in the duplicate denture corresponding to their implant analogs.

The other temporary abutments were installed into the master cast 303, which was picked up using the self-curing acrylic resin. The duplicate denture was then transferred to the fixed interim implant-supported prosthesis, and the excess lengths of the abutments were trimmed below the occlusal plane.

Figure 11:
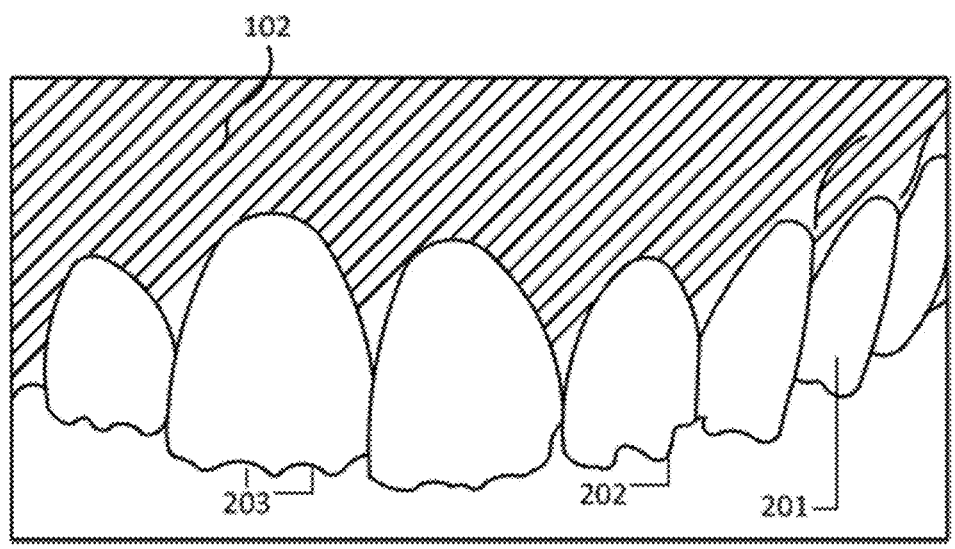
FIG. 11 shows bumps on the incisal edges of the teeth.

FIG. 11 shows the denture teeth are cut back to the enamel layer (approximately 1 mm) to maximize esthetics. A lighter shade of acrylic resin (shade B1) was mixed with self-curing orthodontic acrylic resin (Caulk Orthodontic resin; Dentsply) to build up a more translucent enamel layer.

Figure 12:
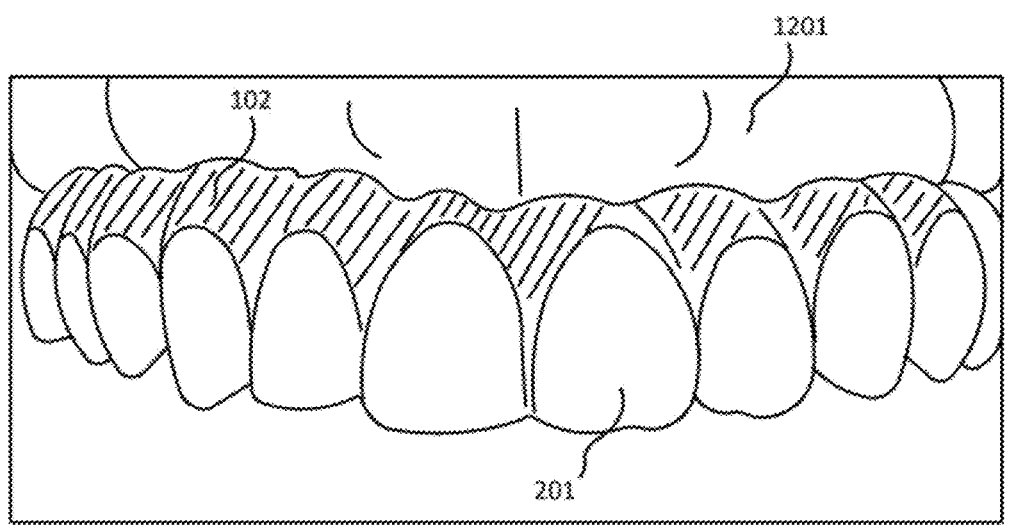
FIG. 12 shows the duplicate denture in the patient's mouth.
Figure 13:
FIG. 13 shows the patient's smile.

The pontic design areas were modified in the fixed interim prosthesis for a modified ridge lap design. The prosthesis was finished and polished using conventional methods. FIG. 12 shows the fixed interim prosthesis in the patient's mouth. A one-screw test confirmed the passive fit of the prosthesis onto the dental implants. FIG. 13 shows the patient smile after the maxillary implant-supported fixed interim prosthesis was delivered against a mandibular complete duplicate denture.

The patient in this study was pleased with the final esthetic results of the prosthesis after including an additional layer of lighter acrylic resin. The duplicate denture was used as a guide for the definitive prosthesis. After two weeks, a putty index for the prosthesis was made on the master casts and sent to a dental laboratory to aid fabrication of the cast metal framework for the definitive hybrid prosthesis. The framework was tested in the patient's mouth to ensure complete seating onto the implants with periapical radiographs and the one-screw test. The framework was sent back to the laboratory to set the acrylic teeth with the same vertical dimensions as the interim prosthesis. During the testing procedure, the CR position and OVD record were verified, and the esthetics was confirmed with the patient. The dental occlusion was adjusted for light anterior guidance with lateral balanced occlusion. The definitive implant-supported hybrid prosthesis was delivered, and the patient was pleased with the final results.

In summary, the disclosed method allows the patient to keep the original denture 108 as a backup and eliminates the possibility of teeth popping out of the original denture 108 when converting it to an implant-supported denture. The method is simple, cost-effective, and produces esthetically pleasing prostheses. Additionally, the esthetics of the prostheses can be modified at any stage of treatment by relining the teeth with acrylic resin. The technique allows for modification of the tooth shade according to patients' preferences, adjustment of the incisal edge position of the maxillary anterior teeth, and re-contouring of the prosthesis depending on the healing process of soft and hard tissues. In fact, as mentioned above, a further and extremely important advantage of the present disclosure is that the wearer of the denture, when handing the latter over to the dentist, only remains without his denture for ten or twenty minutes, after which the denture is returned.

The invention claimed is:

1. A process for forming a duplicate denture, the process comprising:
    obtaining an intermediate denture comprising teeth and a gum portion;
    removing the teeth of the intermediate denture thereby exposing a part of the gum portion;
    applying an adhesive to the exposed part of the gum portion;
    filling a first portion of a mold of an original denture with a first resin;
    placing the gum portion of the intermediate denture into a second portion of the mold;
    placing the first portion and the second portion of the mold in a contiguous matching relationship thereby contacting the exposed part of the gum portion with the first resin; and
    polymerizing the first resin thereby forming a duplicate denture.

2. The process of claim 1, wherein the teeth of the intermediate denture are removed to a gum line of the intermediate denture, and the exposed part of the gum portion comprises a plurality of concave sections angled away from the gum portion.

3. The process of claim 2, wherein the plurality of concave sections comprises a plurality of grooves.

4. The process of claim 3, wherein an average distance between each groove is 1-5 mm.

5. The process of claim 3, wherein each groove is V-shaped or U-shaped.

6. The process of claim 1, wherein the intermediate denture is made by a process comprising:
    filling the mold of the original denture, which has impressions of a tooth portion and a gum portion of the original denture, with a second resin; and
    polymerizing the second resin thereby forming the intermediate denture comprising the teeth and the gum portion.

7. The process of claim 6, wherein the first resin and the second resin comprise an acrylate, nylon, or both.

8. The process of claim 7, wherein the first resin and the second resin comprise the acrylate.

9. The process of claim 8, wherein the first resin and the second resin are independently selected from the group consisting of a heat-curing resin, a self-curing resin, a light-curing resin, and a microwave-curing resin.

10. The process of claim 1, wherein the mold is formed by a process comprising:
    embedding a tooth portion of the original denture in a first molding material;
    embedding a gum portion of the original denture in a second molding material; and setting the first molding material and the second molding material thereby forming the mold.

11. The process of claim 10, wherein the first molding material and the second molding material comprise at least one selected from the group consisting of zinc oxide eugenol, alginate, a polyether, and a silicone.

12. The process of claim 11, wherein the first molding material and the second molding material comprise the silicone.

13. The process of claim 12, wherein the silicone is a condensation-cured silicone.

14. The process of claim 10, wherein the first molding material is placed in a first half of a flask or a first impression tray, and the second molding material is placed in a second half of the flask or a second impression tray.

15. The process of claim 14, wherein the flask is a denture duplicator flask.

16. The process of claim 15, further comprising closing the denture duplicator flask before the setting of the first molding material and the second molding material.

17. The process of claim 1, further comprising:
cutting an incisal edge of at least one tooth in the duplicate denture thereby forming a cut enamel portion; and
applying a third resin and optionally a fourth resin to the cut enamel portion thereby smoothing the at least one tooth.

18. The process of claim 17, wherein the fourth resin is present, the process further comprises mixing the third resin with the fourth resin prior to applying to the cut enamel portion.

19. The process of claim 18, wherein the third resin and the fourth resin comprise an acrylate, nylon, or both.

20. The process of claim 19, wherein the third resin and the fourth resin comprise the acrylate.

* * * * *